United States Patent [19]

Akasaki et al.

[11] Patent Number: 4,833,263

[45] Date of Patent: May 23, 1989

[54] NOVEL ELECTRON-ACCEPTING COMPOUND AND METHOD FOR PREPARING THE SAME

[75] Inventors: Yutaka Akasaki; Katsuhiro Sato; Hiroyuki Tanaka; Katsumi Nukada; Hidemi Sudo, all of Kanagawa, Japan

[73] Assignee: Fuji Xerox Co., Ltd., Tokyo, Japan

[21] Appl. No.: 143,483

[22] Filed: Jan. 13, 1988

[30] Foreign Application Priority Data

Jan. 13, 1987 [JP] Japan .................................... 62-4105

[51] Int. Cl.⁴ ............................................ C07C 121/70
[52] U.S. Cl. ..................................... 558/384; 558/374; 549/213
[58] Field of Search ................................ 558/384, 374

[56] References Cited

U.S. PATENT DOCUMENTS

| | | | |
|---|---|---|---|
| 2,150,154 | 3/1939 | Cope | 558/374 |
| 3,226,388 | 12/1965 | Hartzler | 558/374 X |
| 3,270,045 | 8/1966 | Strobel et al. | 558/374 X |
| 3,549,684 | 12/1970 | Rosin | 558/374 X |
| 3,607,257 | 9/1971 | Johnson | 96/1.6 |
| 3,637,798 | 1/1972 | Sulzberg et al. | 558/374 X |
| 4,207,253 | 6/1980 | Lorenz et al. | 558/374 |
| 4,218,392 | 8/1980 | Lorenz et al. | 558/374 |

FOREIGN PATENT DOCUMENTS 912019 10/1972 Canada .

OTHER PUBLICATIONS

Chemical Abstracts; Subject Index Guide to vol. 56, (1962), p. 89n, "Nomenclature".
Method for Naming All Organic Compound, No. 9.2, p. 69, pub. by Sankyo Shuppan.
Encyclopedia Chimica, vol. 9, p. 89, pub. by Kyoritsu Shuppan.
Encyclopedia Chimica, vol. 1, p. 425, pub. by Kyoritsu Shuppan.

Primary Examiner—Joseph Paul Brust
Attorney, Agent, or Firm—Sughrue, Mion, Zinn, Macpeak & Seas

[57] ABSTRACT

An electron-accepting compound represented by the formula (I):

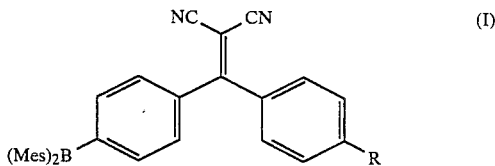

wherein R represents a hydrogen atom or —B(Mes)$_2$ and Mes represents a mesityl group.

A method for preparing an electron-accepting compound represented by the above-described formula (I), which comprises condensing a benzophenone derivative represented by the following formula (II) with malononitride,

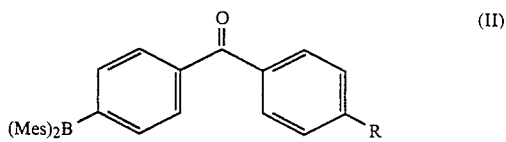

wherein R and Mes have the same meanings as defined for the formula (I).

1 Claim, No Drawings

NOVEL ELECTRON-ACCEPTING COMPOUND AND METHOD FOR PREPARING THE SAME

FIELD OF THE INVENTION

The present invention relates to a novel electron-accepting compound and a method for preparing the same.

BACKGROUND OF THE INVENTION

Various compounds have been known as charge transport agents used in a photoconductive layer of an electrophotographic photoreceptor. The representative compounds are 2,4,7-trinitrofluorenone and compounds containing boron as disclosed, for example, in Japanese Patent Publication No. 9988/73 and Canadian Pat. No. 912,019.

It is desired that an electrophotographic photoreceptor be a positive charging type in view of preventing ozone from being generated in corotoron and of controlling the charging of toners at development. For these purposes, it is necessary that largely effective electron transport agents be used. However, heretofore, such desirable electron transport agents have not yet been found.

The present invention has been developed to provide the desirable electron transport agent in view of the above problem.

SUMMARY OF THE INVENTION

An object of the present invention is to provide an effective electron-accepting compound used as an electron transport agent and a method for preparing the same.

This and other objects have been attained by providing an electron-accepting compound represented by the formula (I);

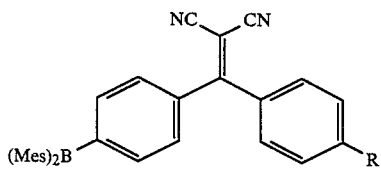

wherein R represents a hydrogen atom or —B(Mes)$_2$ and Mes represents a mesityl group, and by providing a method for preparing an electron accepting compound represented by the formula (I);

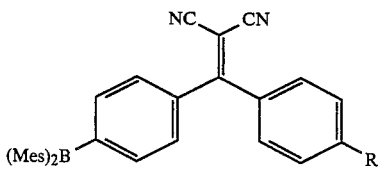

which comprises condensing a benzophenone derivative represented by the formula (II) with malononitrile,

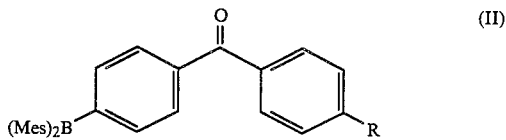

wherein, in both the formulae (I) and (II), R represents a hydrogen atom or —B(Mes)$_2$ and Mes represents a mesityl group.

DETAILED DESCRIPTION OF THE INVENTION

As a result of extensive research, the inventors of the present invention synthesized a novel boron-containing compound and found that it is an effective electron-accepting compound as an electron transport agent and thus attained the present invention.

The novel electron-accepting compound of the present invention is represented by the formula (I):

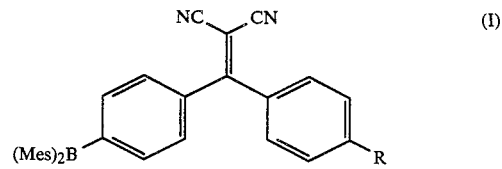

wherein R represents a hydrogen atom or —B(Mes)$_2$ and Mes represents a mesityl group.

The above compound of the present invention can be prepared by condensing benzophenone derivatives represented by the formula (II) with malononitrile,

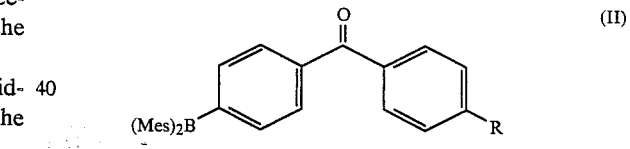

wherein R has the same definition as above.

The present invention will be hereinafter described in more detail.

In the present invention, the condensation reaction of 4-dimesitylborobenzophenone or 4,4'-bis-dimesitylborobenzophenone with malononitrile is carried out in a solvent at a temperature of from 50° C. to the boiling poing of the solvent, in the presence of a catalyst, if desired.

Suitable solvents include pyridine; aromatic hydrocarbons such as benzene, toluene or xylene; polar solvents such as N,N-dimethyl formaldehyde, N,N-dimethyl acetamide, N-methyl-2-pyrrolidone or dimethyl sulfoxide; halogenated solvents such as CHCl$_3$; alcohols such as methanol and ethanol; and ethers such as tetrahydrofuran. These solvents may be used in mixture. Among these, pyridine is particularly preferred, because pyridine does not need a catalyst. Further, when aromatic hydrocarbons are employed, it is preferred that the reaction is carried out while water generated from the reaction is being removed as a constant boiling mixture with a solvent, thereby allowing the reaction to proceed more easily.

Suitable catalyst include ammonium, organic amines such as diethylamine, benzylamine, piperidine or morpholine, or acetic acid salts thereof, or Lewis acid such as TiCl$_4$.

The preferable combinations of the solvents and the catalysts described above are a combination of alcohols such as methanol and ethanol and piperidine, or a combination of halogenated solvents such as CHCl$_3$ and pyridine and Lewis acid such as TiCl$_4$.

4-Dimesitylborobenzophenone or 4,4′-bis-dimesityl borobenzophenone used as a starting material in the present invention is synthesized in the following manner.

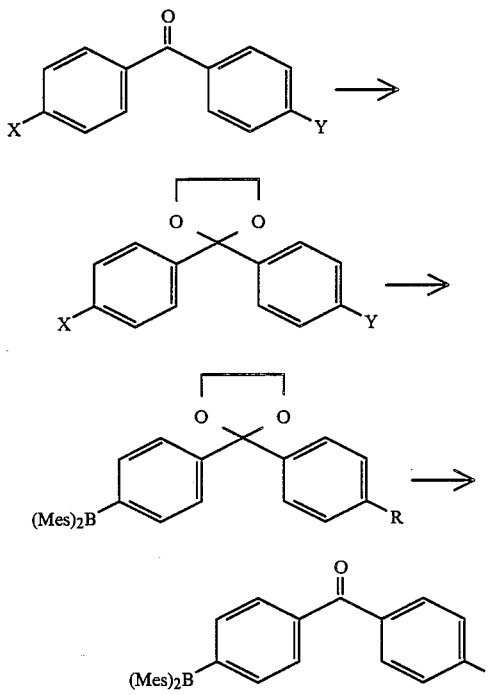

In the formulae, X represents a halogen atom, Y represents a hydrogen atom or a halogen atom, and R has the same definition as above.

More specifically, 4-halogenobenzophenone or 4,4′-dihalogenobenzophenone represented by the formula (III) and ethylene glycol are refluxed at from room temperature (from about 10° to 30° C.) to a boiling point of the solvent in the presence of organic sulfonic acid in a small amount in an organic solvent such as benzene or toluene to form an ethylene ketal represented by the formula (IV).

The resulting ethylene ketal is reacted with dimesitylboron fluoride to synthesize the compound represented by the formula (V) using the reaction method of (1) Grignard reaction or (2) halogen metal exchange reaction.

The following reaction occurs using the Grignard reaction of method (1).

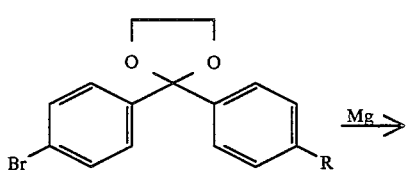

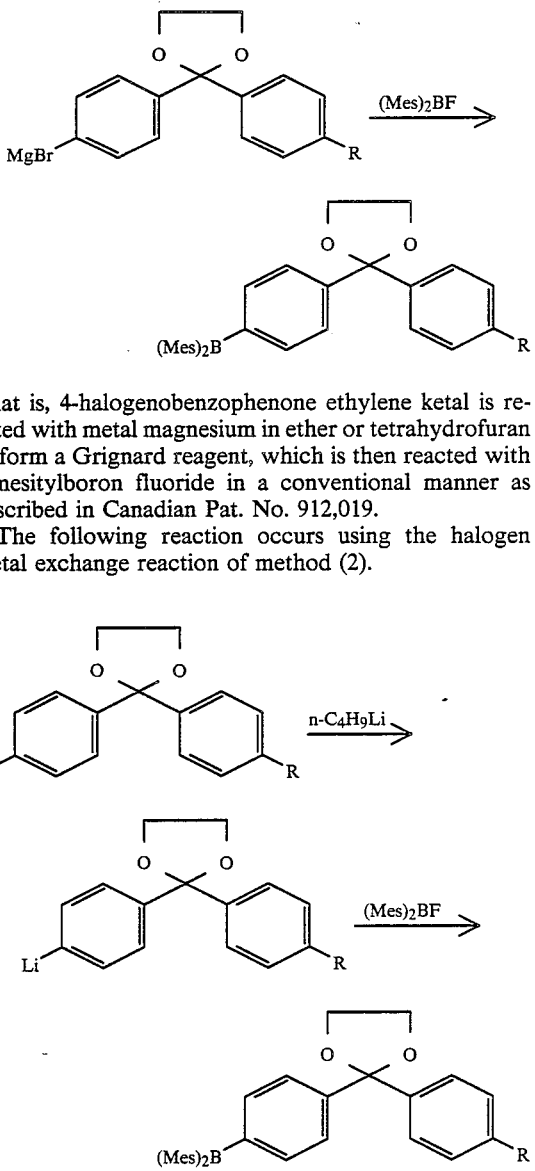

That is, 4-halogenobenzophenone ethylene ketal is reacted with metal magnesium in ether or tetrahydrofuran to form a Grignard reagent, which is then reacted with dimesitylboron fluoride in a conventional manner as described in Canadian Pat. No. 912,019.

The following reaction occurs using the halogen metal exchange reaction of method (2).

That is, as described in Canadian Pat. No. 912,019, 4-halogenobenzophenone ethylene ketal is reacted with an alkyl lithium compound such as n-butyl lithium in a solvent such as ether or petroleum ether at from −70° C. to 40° C. to form 4-lithium benzophenone ethylene ketal, which is then reacted with dimesitylboron fluoride. Employment of reaction (2) is more favorable because it has higher reactivity.

Ethylene ketal represented by the formula (V) is refluxed at from room temperature (from about 10° to 30° C.) to a boiling point of the solvent in the presence of mineral acid such as hydrochloric acid in a solvent such as methanol, ethanol or dimethyl ketone to synthesize the starting material of the present invention as represented by the formula (II).

The electron accepting compound of the present invention represented by the formula (I) is effective as a sensitizing agent or an electron transport agent for an electrophotographic photoreceptor. That is, in the case that a light-sensitive (photoreceptive) layer provided on an electroconductive support has a single layer structure, the electron accepting compound of the present invention is used as a sensitizing agent. In the case that a photoreceptive layer has a laminated layer structure having a charge-generating layer and a charge transport layer, the electron-accepting compound of the present invention is used as an electron transport agent in a charge transport layer.

The present invention will be illustrated in more detail by the examples, applied examples and comparative examples, which are not intended to be limiting.

EXAMPLE 1

4-Bromobenzophenone: 25 g
Ethylene glycol: 50 g
p-Toluenesulfonic acid: 1.8 g

The above composition was refluxed in 800 ml of toluene for 20 hours and was washed completely with diluted $Na_2CO_3$ solution and was then washed with water. It was dried with $Na_2SO_4$ and the solvent was removed. The residue was recrystallized with MeOH (methanol) to obtain 15 g of 4-bromobenzophenone ethylene ketal. m.p. 54° to 56° C.

8.0 g of 4-bromobenzophenone ethylene ketal was stirred under a nitrogen gas flow in 100 ml of ether, 16 ml and a hexane solution of n-$C_4H_9Li$ (1.72 mol concentration) was added thereto and stirred at room temperature (from about 10° to 30° C.) for 5 minutes. Then, a solution of 8.8 g of dimesitylboron fluoride [$(Mes)_2BF$] having been dissolved in 100 ml of ether was added thereto as soon as possible. Dimesitylboron fluoride [$(Mes)_2BF$] used in this example was synthesized in the same manner as disclosed in Canadian Pat. No. 912,019. After dimesitylboron fluoride was added, the mixture was refluxed for 2.5 hours, cooled and added with 200 ml of water to separate an ether phase and additionally a water phase was extracted twice with 30 ml of methylene chloride. Organic phase was wholly dried and the solvent was removed under reduced pressure. The residue was refluxed in 400 ml of ethanol, 20 ml of water and 20 ml of concentrated hydrochloric acid for 5 hours and then 500 ml of water was added. The precipitated crystals were separated and recrystallized with methanol/hexane to obtain 7 g of 4-dimesitylborobenzophenone.

1.5 g of 4-dimesitylborobenzophenone and 0.75 g of malononitrile were refluxed under a nitrogen gas flow in 30 ml of pyridine for 8 hours. Thereafter, pyridine was removed under reduced pressure, the residue was dissolved in methylene chloride and then was dried, and methylene chloride was removed under reduced pressure. The residue was recrystallized with methanol/$CH_2Cl_2$ to obtain 1.1 g of the desired compound (No. 1) wherein R in the formula (I) represents a hydrogen atom.

m.p.: 159° to 160° C.
Mass Spectrum: M+ 478
Elemental Analysis:

|  | C | H | N |
| --- | --- | --- | --- |
| Calculated value: | 85.36 | 6.53 | 5.86 |
| Measured value: | 85.50 | 6.35 | 5.93 |

IR: 2,224 $cm^{-1}$ (KBr)
NMR: 7.60–7.15 ppm (Ar, 9H), 6.76 ppm (s, 4H), 2.26 ppm (s, 6H), 1.95 ppm (s, 12H), ($CDCl_3$)

EXAMPLE 2

4,4'-Dibromobenzophenone: 20 g
Ethylene glycol: 50 g
p-Toluenesulfonic acid: 1.8 g The above composition was refluxed in 800 ml of toluene for 20 hours and processed in the same manner as in Example 1 to obtain 13 g of 4,4'-dibromobenzophenone ethylene ketal (recrystallized with ethanol). m.p. 103° to 104° C.

6.0 g of 4,4'-dibromobenzophenone ethylene ketal was stirred under a nitrogen gas flow in 100 ml of ether, and 19.2 ml of a hexane solution of n-$C_4H_9Li$ (1.72 mol concentration) was added thereto, and after stirring at room temperature (from about 10° to 30° C.) for 5 minutes, 100 ml of an ether solution of 8.7 g of $(Mes)_2BF$ was added thereto quickly and refluxed for 2.5 hours. Thereafter, the mixture was processed in the same manner as in Example 1 to obtain 7.3 g of 4,4'-bisdimesitylborobenzophenone (recrystallized with ethanol/$CH_2Cl_2$). m.p. 130° to 140° C.

7 g of 4,4'-bisdimesitylborobenzophenone and 1.4 g of malononitrile were refluxed in 100 ml of pyridine for 8 hours, and then the same procedure as in Example 1 was repeated to obtain 5.2 g of the desired compound (No. 2) (recrystallized with $CH_2Cl_2$/methanol) wherein R in the formula (I) represents —$B(Mes)_2$.

m.p: 245° to 247.5° C.
Mass Spectrum: M+ 727
Elemental Analysis:

|  | C | H | N |
| --- | --- | --- | --- |
| Calculated value: | 85.96 | 7.21 | 3.86 |
| Measured value: | 85.57 | 7.24 | 3.73 |

IR: 2,224 $cm^{-1}$ (KBr)
NMR: 7.55 ppm (d, 4H), 7.32 ppm (d, 4H), 6.78 ppm (s, 8H), 2.29 ppm (s, 12H), 1.96 ppm (s, 24H), ($CDCl_3$)

APPLIED EXAMPLE 1

A charge generating layer (2.5 μm) composed of trigonal system-Se/polyvinylcarbazole (trigonal-Se 70 wt%) was provided on an electroconductive support, and a solution wherein 0.5 g of compound No. 1, and 0.75 g of bisphenol A polycarbonate (Macroron 5705, produced by Bayer Co., Ltd.) were dissolved in 7 g of methylene chloride was coated thereon with a gap of 5 mil under moistened condition (that is, the solution was coated on the support with a gap of applicator of 5 mil) and dried at 80° C. for 1 hour to separate an electrophotographic photoreceptor. The thus-obtained photoreceptor was charged with +800 V or −800 V by an electrostatic copy paper testing machine ("SP428", manufactured by Kawaguchi Riken Co., Ltd.), and exposed to white light of 5 luxes to measure its sensitivity.

| Charging potential | +800 V | −800 V |
| --- | --- | --- |
| Initial sensitivity dV/dt (V/sec) | 75 | — |

APPLIED EXAMPLE 2

The same procedure as in Applied Example 1 was repeated to prepare an electrophotographic photoreceptor except that compound No. 2 was used.

APPLIED EXAMPLE 3

A solution wherein 0.5 g of compound No. 1 and 0.75 g of polyvinylcarbazole were dissolved in 7 g of methylene chloride was coated on an electroconductive support with a gap of 5 mil under the moistened condition (that is, the solution was coated on the support with a gap of applicator of 5 mil) and dried at 80° C. for 1 hour to obtain an electrophotographic photoreceptor.

APPLIED EXAMPLE 4

The same procedure as in Applied Example 3 was repeated to obtain an electrophotographic photoreceptor except that compound No. 2 was used.

COMPARATIVE EXAMPLE 1

The same procedure as in Applied Example 1 was repeated to obtain an electrophotographic photoreceptor except that 2,4,7-trinitrofluorenone (hereinafter abbreviated as TNF) was used.

COMPARATIVE EXAMPLE 2

The same procedure as in Applied Example 3 was repeated to obtain an electrophotographic photoreceptor except that TNF was used.

The thus-obtained electrophotographic photoreceptors were charged and exposed and their initial sensitivities measured as described in Applied Example 1. The initial sensitivities (dV/dt) at a charging potential of +800 V and −800 V are shown below.

|  | Compound | dV/dt +800 V | dV/dt −800 V |
| --- | --- | --- | --- |
| Applied Example 2 | No. 2 | 83 | — |
| Comparative Example 1 | TNF | 66 | — |
| Applied Example 3 | No. 1 | 182 | 184 |
| Applied Example 4 | No. 2 | 205 | 173 |
| Comparative Example 2 | TNF | 154 | 165 |

The electron-accepting compound represented by the formula (I) in the present invention is a novel compound which has never been disclosed in any references and is effective as a sensitizing agent or an electron transport agent in an electrophotographic photoreceptor. It exhibits excellent electrophotographic characteristics particularly when it is used as an electron transport agent in a positive charging type electrophotographic photoreceptor having a laminated layer containing a charge generating layer and a charge transport layer provided on an electroconductive support in this order.

While the invention has been described in detail and with reference to specific embodiments thereof, it will be apparent to one skilled in the art that various changes and modifications can be made therein without departing from the spirit and scope thereof.

What is claimed is:

1. An electron-accepting compound represented by the formula (I):

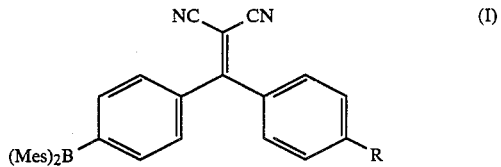

wherein R represents a hydrogen atom or —B(Mes)$_2$ and Mes represents a 2,4,6—(CH$_3$)$_3$C$_6$H$_2$— group.

* * * * *